(12) United States Patent
Uyehara et al.

(10) Patent No.: US 7,295,003 B2
(45) Date of Patent: Nov. 13, 2007

(54) NON-DESTRUCTIVE TESTING SYSTEM AND METHOD UTILIZING A MAGNETIC FIELD TO IDENTIFY DEFECTS IN A LAYER OF A LAMINATED MATERIAL

(75) Inventors: Clyde T. Uyehara, Kent, WA (US); James C. Kennedy, Renton, WA (US); Carl B. Gifford, Buckley, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 10/946,107

(22) Filed: Sep. 22, 2004

(65) Prior Publication Data

US 2006/0061357 A1   Mar. 23, 2006

(51) Int. Cl.
 *G01N 27/90* (2006.01)
(52) U.S. Cl. .................... 324/219; 324/240
(58) Field of Classification Search ........ 324/219–221, 324/237, 238, 240, 241–243, 262; 73/866.5
See application file for complete search history.

(56) References Cited

U.S. PATENT DOCUMENTS

| | | | | |
|---|---|---|---|---|
| 2,103,256 A * | 12/1937 | Greenslade | .................. | 324/219 |
| 2,104,643 A * | 1/1938 | Greenslade | .................. | 324/219 |
| 4,084,136 A * | 4/1978 | Libby et al. | ................ | 324/238 |
| 4,268,791 A * | 5/1981 | Rogel et al. | ................ | 324/238 |
| 4,279,163 A * | 7/1981 | Takekoshi et al. | ............ | 73/761 |
| 4,706,020 A * | 11/1987 | Viertl et al. | ................ | 324/238 |
| 4,727,322 A * | 2/1988 | Lonchampt et al. | ....... | 324/229 |
| 4,954,777 A | 9/1990 | Klopfer et al. | ............. | 324/232 |
| 5,136,240 A * | 8/1992 | Geier et al. | ................. | 324/220 |
| 5,172,058 A * | 12/1992 | Tasca | .......................... | 324/225 |
| 5,291,136 A * | 3/1994 | Van der Veer et al. | ..... | 324/262 |
| 5,465,045 A * | 11/1995 | DeRock | ....................... | 324/220 |
| 5,554,933 A * | 9/1996 | Logue | .......................... | 324/233 |
| 5,834,937 A * | 11/1998 | Burris | ......................... | 324/219 |
| 5,903,147 A * | 5/1999 | Granger et al. | ............. | 324/219 |
| 5,914,596 A | 6/1999 | Weinbaum | .................. | 324/228 |
| 5,942,894 A | 8/1999 | Wincheski et al. | ......... | 324/220 |
| 6,496,713 B2 * | 12/2002 | Avrin et al. | ................ | 600/409 |
| 6,784,662 B2 * | 8/2004 | Schlicker et al. | ........... | 324/242 |
| 6,798,198 B2 * | 9/2004 | Tsukernik et al. | .......... | 324/262 |

FOREIGN PATENT DOCUMENTS

| | | | |
|---|---|---|---|
| CA | 2 088 749 | | 7/2003 |
| EP | 0 792 455 | | 4/2000 |
| JP | 03262959 | * | 11/1991 |
| JP | 403261856 | * | 11/1991 |
| WO | 96/15445 | | 5/1996 |

* cited by examiner

*Primary Examiner*—Jay M Patidar
(74) *Attorney, Agent, or Firm*—Baker & Hostetler LLP

(57) ABSTRACT

Techniques for detecting defects in the proximity of a hole of a laminate structure include inserting a generally cylindrical body portion into a hole such that a first coil of wire will reside in a plane substantially parallel to a first electrically conductive layer of the laminate material. A magnetic field produced by the first coil of wire will produce eddy-currents in the conductive layer in the plane of the first conductive layer, but damaged laminate materials will fail to produce similar eddy-currents. As the differences in eddy-currents between damages and undamaged laminate layers can be measured, damage to such laminate materials can be determined.

13 Claims, 10 Drawing Sheets

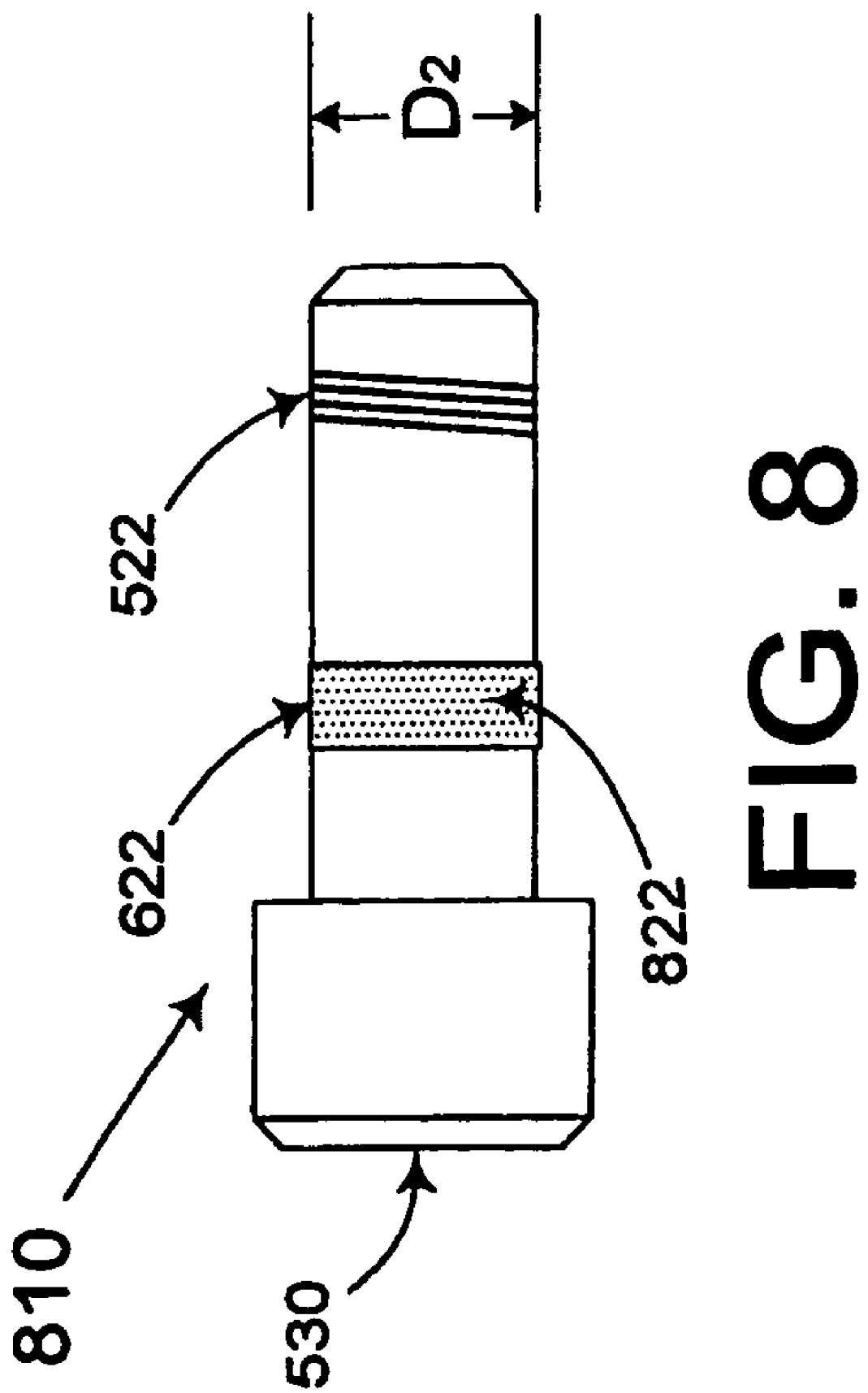

NON-DESTRUCTIVE TESTING SYSTEM AND METHOD UTILIZING A MAGNETIC FIELD TO IDENTIFY DEFECTS IN A LAYER OF A LAMINATED MATERIAL

FIELD OF THE INVENTION

This invention relates to methods and systems for non-destructive testing of materials.

BACKGROUND OF THE INVENTION

Originally, naturally available and relatively light materials, such as wood, were the most common materials used for constructing aircraft. However, with the development of new alloys the aircraft construction industry shifted from one of carpentry to one of metal shaping.

Relatively recently, a new generation of materials known as "composites" or "composite materials" were developed. Certain composite materials often provide an excellent strength-to-weight ratio as compared to metals, and their acceptance into the various aircraft industries is near universal.

Generally, there are two major genres of composite materials: honeycomb structures and laminates. Honeycomb structures are exceeding light materials that provide unequalled structural support (for their weight) when placed in wings and other strategic locations in a given aircraft. Laminate materials, while usually not as light as honeycomb structures, are often lighter than any commercially viable metal equivalent, and typically far stronger than any honeycomb structure.

As with all materials, laminates are subject to the normal "wear and tear" of everyday use. For example, over the course of everyday usage, cracks and other defects can develop around laminate-mechanical interfaces, such as bolt-holes. Such damage can not always be seen. While various diagnostic tools, such as ultrasonic imagers, are available to assess such hidden damage, these existing tools can be very expensive and require a substantial amount of training to properly use. Accordingly, new methods and systems for detecting damage in laminate structures are desirable.

SUMMARY OF THE INVENTION

In one aspect, an apparatus for detecting defects in the proximity of a hole of a laminate structure includes a generally cylindrical body portion having a diameter substantially close to the diameter of the hole and capable of being inserted into the hole, and a first coil of wire wrapped about the cylindrical body portion such that, when the body portion is inserted into the hole, the first coil of wire resides in a plane substantially parallel to a first electrically conductive layer of the laminate material such that a magnetic field produced by the first coil of wire will produce eddy-currents in the first conductive layer in the plane of the first conductive layer.

In another aspect, an apparatus for detecting defects in the proximity of a hole of a laminate structure includes a generally cylindrical body portion having a diameter substantially close in the diameter of the hole and capable of being inserted into the hole, and one or more first coils embedded within the body portion with each of the first coils having a portion residing at or near the surface of the body portion at different angular ranges, where each angular range is less than 360

In still another aspect, a method of diagnosing a crack in the proximity of a hole of a laminate structure includes positioning a first coil in the hole with the first coil residing in a plane substantially parallel to the plane of the electrically conductive layer, exciting the first coil in a manner as to produce appreciable eddy-currents flowing in the plane of the electrically conductive layer, and measuring the impedance of the first coil, wherein the impedance of the first coil changes as a function of eddy-current activity occurring close to the first coil.

In yet another aspect, an apparatus for detecting defects in the proximity of a hole of a laminate structure includes a first body and an inducing means for inducing eddy-currents coupled to the first body, and a measuring means for measuring an impedance of the inducing means.

There has thus been outlined, rather broadly, certain embodiments of the invention in order that the detailed description thereof herein may be better understood, and in order that the present contribution to the art may be better appreciated. There are, of course, additional embodiments of the invention that will be described or referred to below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 8 depicts an exemplary third bolt-hole probe.

DETAILED DESCRIPTION

Figure 1:
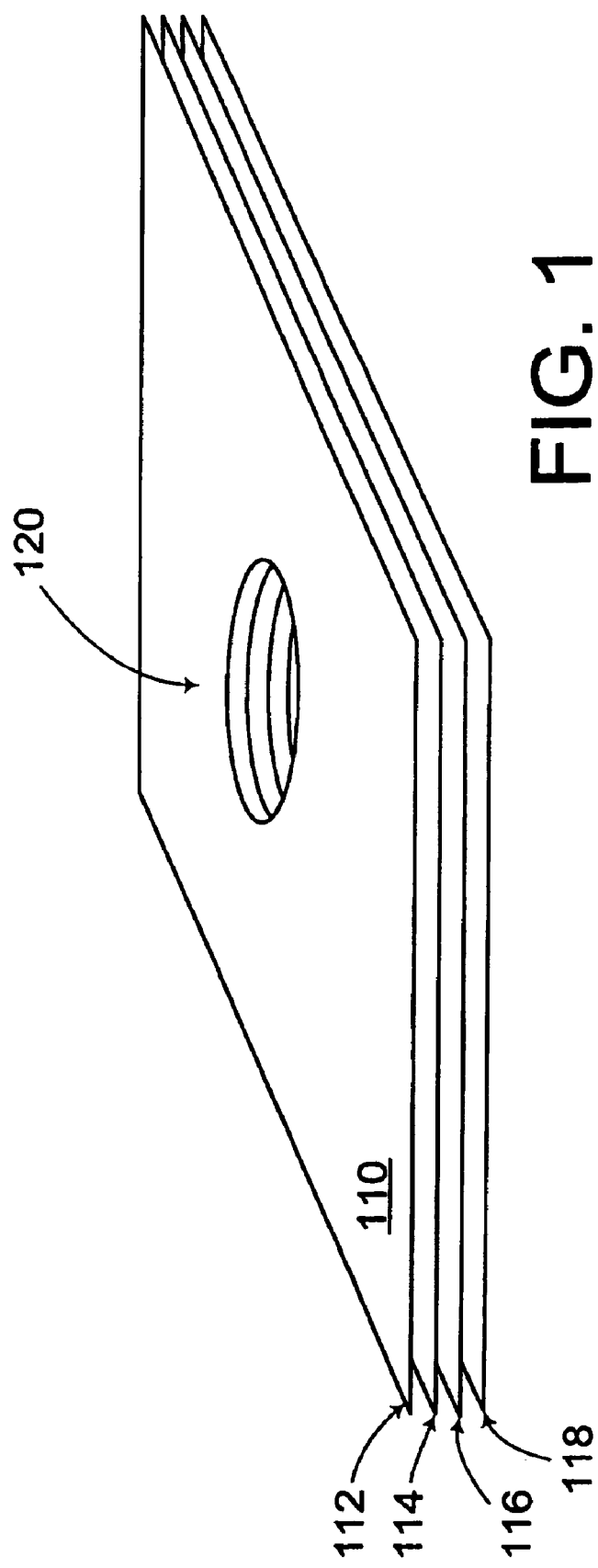
FIG. 1 depicts a laminate material with a bolt-hole.

The disclosed methods and systems provide new diagnostic tools for relatively new materials. FIG. 1 depicts one such material known as a laminate. The laminate structure 110 of FIG. 1 includes four laminate layers 112-118, and further includes a bolt-hole 120 in the center. While a bolt-hole is generally defined by its purpose as well as its structure, for the purpose of this disclosure, a "bolt-hole" can be any through-hole in a laminate structure whether or not the hole is ultimately used in conjunction with bolts. The laminate structure 110 of FIG. 1 can be composed of any number of known or later developed material, such as carbon-fiber, titanium, titanium alloy etc, some of which can conduct electricity.

While many laminate layer materials are conductive, it should be appreciated that the great majority of bonding materials used to join laminate layers are typically ester-based resin and other poor conductors. Accordingly, it should be appreciated that the vast majority of laminate structures will only conduct electricity well in the individual thin planes of its laminate layers. Conductivity between layers, i.e., across the thickness of a laminate structure, will be poor or nonexistent.

Figure 2:
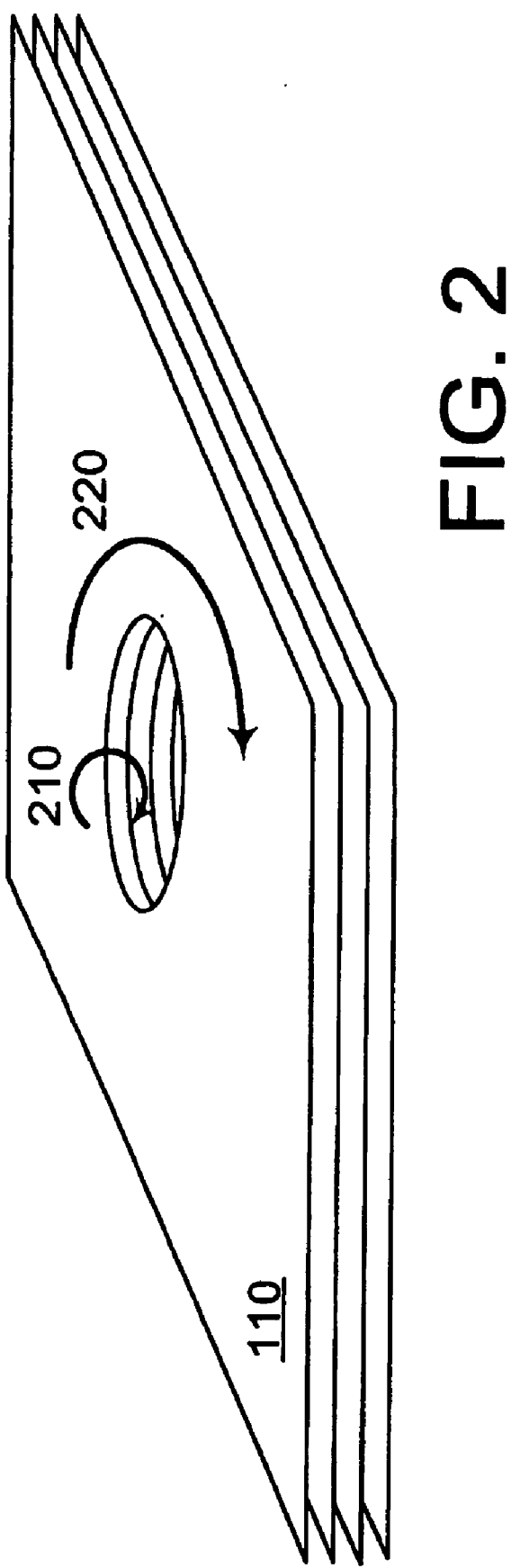
FIG. 2 depicts possible eddy-current paths in the laminate material of FIG. 1.

FIG. 2 depicts various eddy-currents that might be induced into the laminate structure 110 of FIG. 1. As shown in FIG. 2, a first eddy-current 220 is capable of flowing in the plane of the top laminate layer. Assuming that the top-layer is conductive, an incumbent magnetic field of the proper orientation can easily generate such eddy-currents.

While a second eddy-current 210 is also depicted as flowing in a direction perpendicular to the plane of the top laminate layer, the path of the second eddy-current 210 is limited to the thickness of a layer, which may be but a few 100ths of an inch. As a result, even a strong and correctly oriented magnetic field is likely to induce but a minute amount of current in the path of eddy-current 210.

Figure 3:
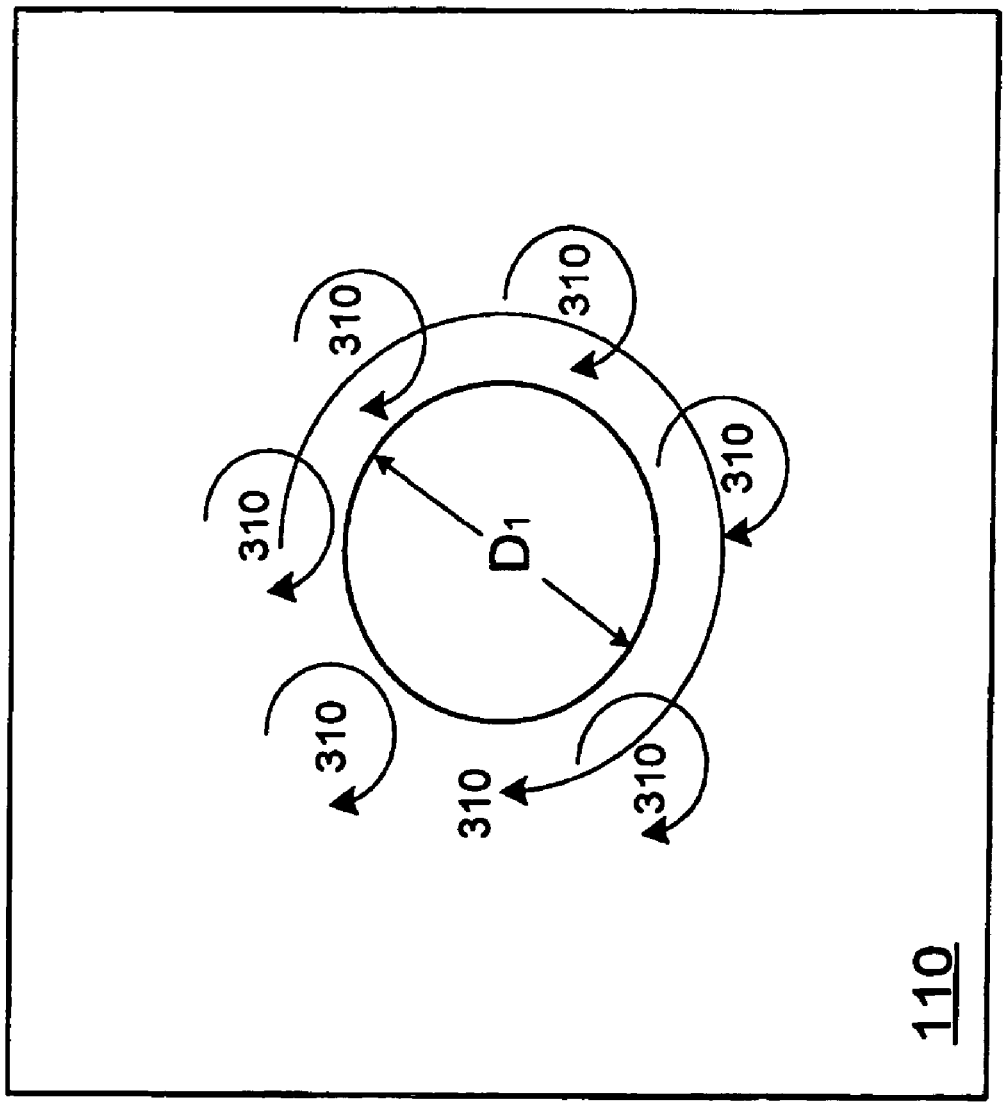
FIG. 3 depicts eddy-current paths in an undamaged laminate material.
Figure 4:
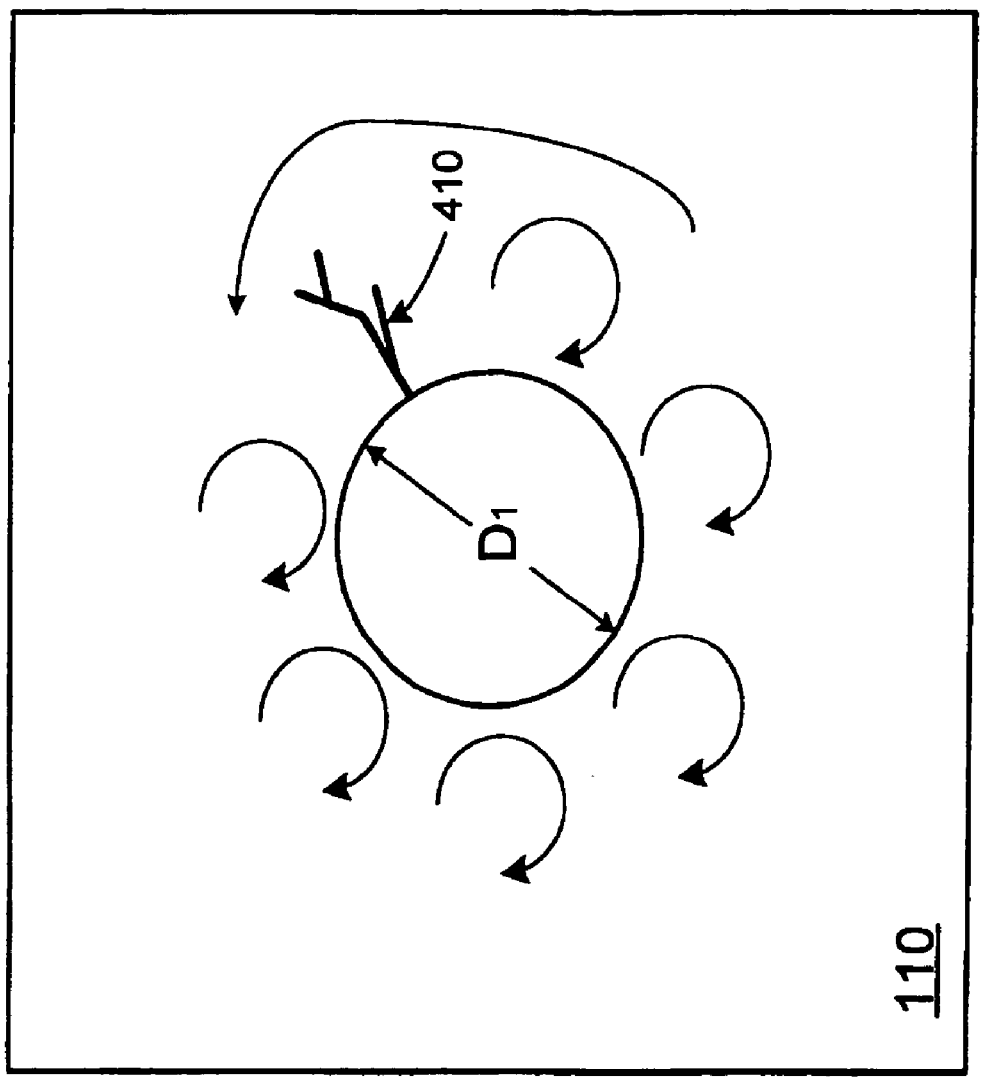
FIG. 4 depicts eddy-current paths in a damaged laminate material.

FIG. 3 better depicts the eddy-current activity that can be generated using an appropriately configured magnetic field, i.e., a magnetic field having lines of flux extending in a direction perpendicular to the plane of structure 110. As shown in FIG. 3, eddy-currents 310 travel in closed paths, which will be generally circular when current is unimpeded. In contrast, FIG. 4 depicts the resultant eddy-current activity when a conductive plane is damaged of flawed. As is depicted in FIG. 4, crack 410 can impede any local, smaller eddy-currents and/or cause the paths of larger eddy currents to change dramatically.

Figure 5B:
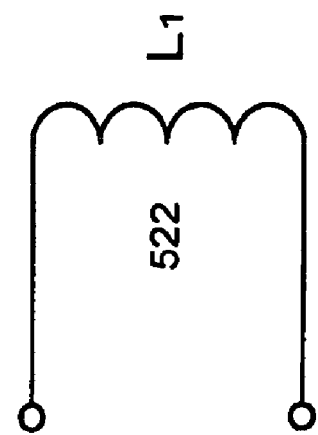
FIG. 5B depicts the circuitry of the first bolt-hole probe.
Figure 5A:
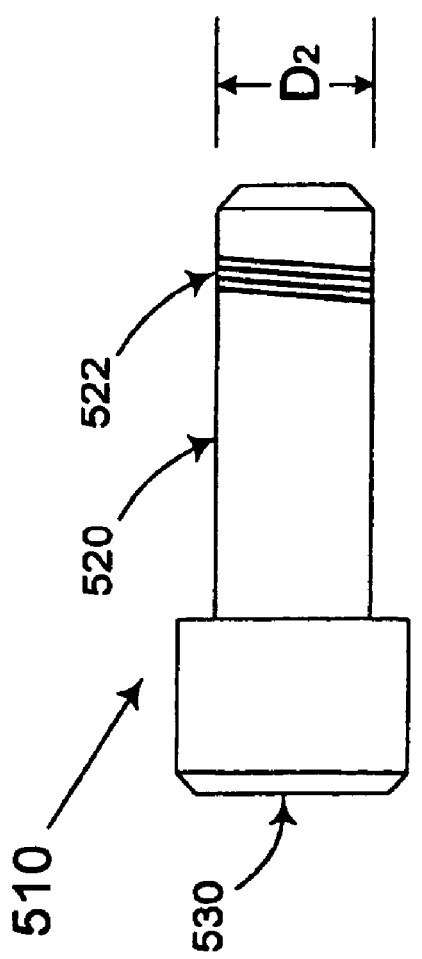
FIG. 5A depicts a first bolt-hole probe useful for detecting bolt-hole damage.

FIG. 5A depicts a first testing-device 510 capable of diagnosing flaws/damage in the vicinity of a bolt-hole of a laminate structure. Generally, the testing-device 510 operates by inducing appreciable eddy-currents in the plane of a laminate structure and detecting whether the expected amounts of eddy-currents are present. As shown in FIG. 5A, testing-device 510 has a cylindrical main body portion 510 and a test-coil 522 wrapped around the body portion 520 and slightly inset such that the test-coil 522 is flush or slightly inset of the body portion 520. The testing-device 510 further includes a head portion 530. The diameter of the body portion D2 can be slightly less than the diameter of a bolt-hole for which the testing-device 510 is designed to make insertion possible but still keep the coil 522 as close to the inner-wall of the bolt-hole as possible. As shown in FIG. 5B, the coil 522 is primarily an inductor capable of generating a magnetic field.

In operation, coil 522 can be excited with any of a range of frequencies such that, when place in the plane of a conductive laminate layer, the coil 522 will induce eddy-currents about the plane of the laminate material. As discussed above with respect to FIGS. 1-4, the eddy-currents induced in an undamaged laminate layer will vary from those of a damaged layer. That is, as the inductance of a coil will generally vary when place in different environment, and the eddy-current paths of damaged and undamaged laminate layers will produce different environments from one another, it should be appreciated that the impedance across the coil 522 will be different when placed in the plane of an undamaged laminate layer as compared to when placed in the plane of a damaged laminate layer.

Accordingly, by comparing the impedance across the coil 522 with some form of reference(s), the testing device 510 can determine whether the coil is in free space, placed next to an undamaged laminate layer of a known material or placed next to a damaged laminate layer. Further, by employing the appropriate resolution and using a variety of references (or meter), it can be possible to determine whether any damage to a laminate layer is slight, appreciable or severe. Still further, by measuring the depth of the coil 522 as placed within a bolt-hole, the particular layer, as well as the damaged, can be determined.

Figure 6A:
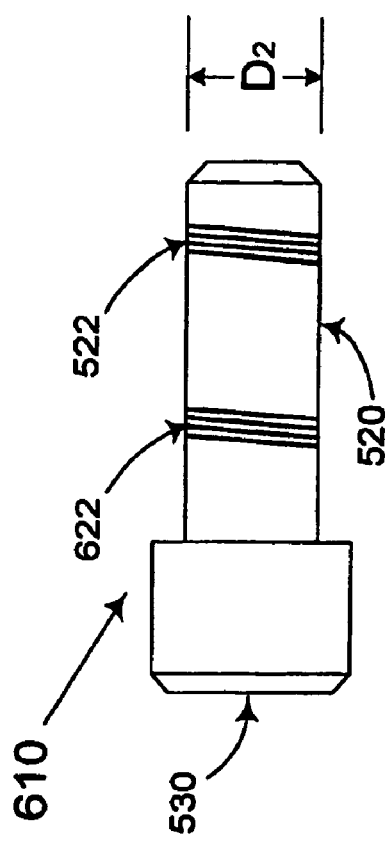
FIG. 6A depicts a second bolt-hole probe useful for detecting bolt-hole damage.

FIG. 6A depicts a second testing-device 610 capable of detecting flaws/damage in the vicinity of a bolt-hole of a laminate structure. As with the device of FIG. 5A, the second testing-device 610 has a main body portion 510 and a test-coil 522 wrapped around the body portion 520. However, unlike the device of FIG. 5A, the second testing-device 610 further includes a second coil 622 that can act as a reference to the first coil 522. That is, by employing a reference-coil that has the same resistive and reactive properties as a test-coil, and exciting both coils using the same frequency signals, the impedance of the reference-coil should track the impedance of the test-coil barring certain external factors. Such external factors include, for example, differences in temperature, external magnetic fields and proximity to conductive materials can change the relative impedance of two or more coils that might otherwise be identical.

In view of such external factors, it should be appreciated that the material used for the body 520 should be a good conductor of heat to keep temperatures relatively even. While metals are good conductors of heat and can provide shielding against wayward electromagnetic interference, tests have shown that better performance can be had by using a body made from materials that are highly conductive of heat, but poor conductors of electricity. One plastic that has proved useful is Delrin (any of a number of acetal polyoxymethylene (POM) resins) due to its conduction properties, its high strength and stiffness, dimensional stability and low friction/high wear.

Figure 6B:
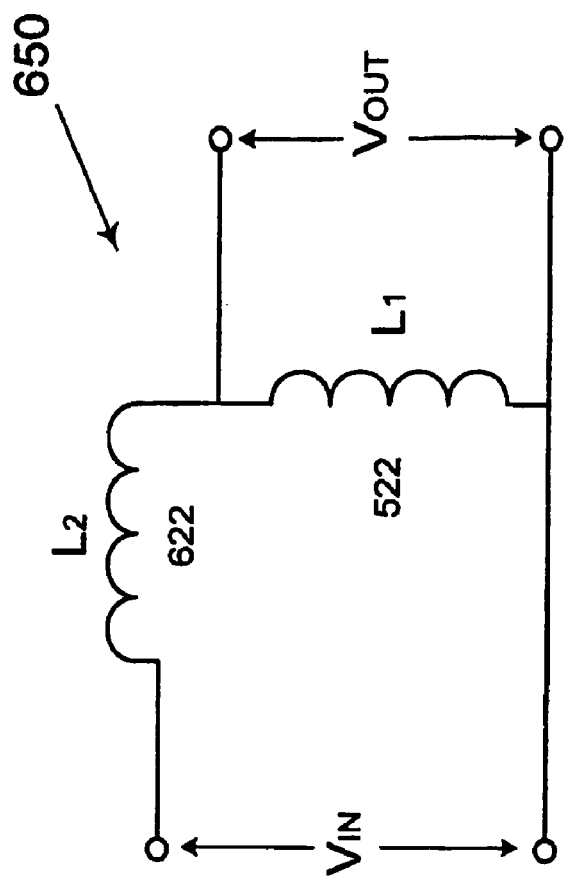
FIG. 6B depicts the circuitry of the second bolt-hole probe.

FIG. 6B depicts a useful circuit configuration for use in certain sensors known as a "bridge" or a "voltage divider". The exemplary bridge 650 is constructed of coils 522 and 622 having respective inductances $L_1$ and $L_2$. When $L_1$ and $L_2$ are known, Vout can be a determinable fraction of Vin. As the impedance of coil 522 is expected to deterministically change when placed in the vicinity of an undamaged conductive laminate structure, the ratio of Vout/Vin also will change deterministically. In contrast, when coil 522 is placed in the vicinity of a damaged conductive laminate structure, the impedance of coil 522 will not change as it would when placed near an undamaged laminate structure. That is, the ratio of Vout/Vin (damaged structure) will not likely equal Vout/Vin (undamaged structure). Given that the temperature and other external factors to coils 522 and 622 are expected to remain nearly identical, the bridge 650 of FIG. 6B presents itself as an extremely useful instrument for measuring induced eddy-current activity, and thus useful for determining damage for conductive laminate layers.

Figure 7A:
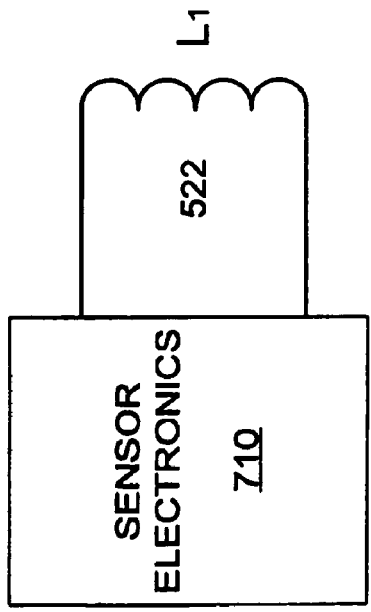
FIG. 7A depicts an exemplary circuit interface for the first bolt-hole probe.

FIG. 7A depicts a schematic of the test-coil 522 of FIG. 5A together with an appropriately designed sensor circuitry 710. The exemplary sensor circuitry 710 can be designed to excite coil 522 with a voltage having a sinusoidal frequency $f_1$ and measure the impedance of the coil 522 under such conditions. In the present embodiment, the driving circuitry (not shown) has a characteristic impedance $X_1$. As the impedance of an inductor will vary with frequency, it should be appreciated that the impedance of the coil 522 can be made to match the impedance of the driving circuitry if frequency $f_1$, is chosen to be $X_1/2\pi L_1$, where $L_1$ is the inductance of coil 522. By matching the impedances, the performance of the testing device as a whole can be expected to improve.

Figure 7B:
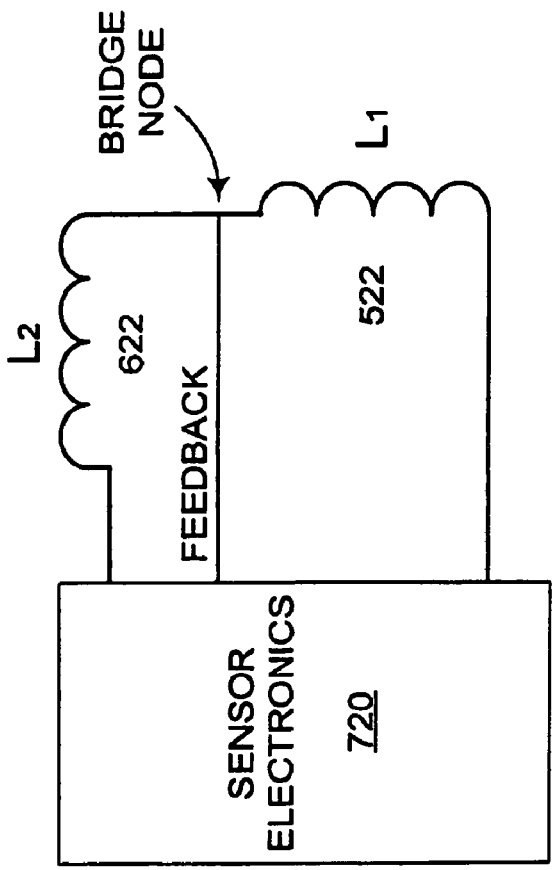
FIG. 7B depicts an exemplary circuit interface for the second bolt-hole probe.

FIG. 7B depicts a schematic of the test-coil of FIG. 6A together with a second appropriately designed sensor circuitry 720 designed to excite coils 522 and 622 with a voltage having a sinusoidal frequency $f_2$ while measuring the voltage of the bridge node between the two coils 522 and 622. As with the circuit in FIG. 7A, the sensor circuit's driving circuitry has a characteristic impedance $X_2$, and it can be beneficial to match the impedance of the coils 522 and 622 with the impedance of the driving circuitry. Assuming the bridge node between the two coils 522 and 622 is high-impedance, the optimal frequency $f_2$ can be expected to be $X_2/2\pi(L_1+L_2)$ where $L_1$ and $L_2$ are the respective inductances of coils 522 and 622. Should the feedback node be a lower impedance, the optimal frequency $f_2$ may vary but it can still be a function of $L_1$ and $L_2$. With respect to FIGS. 7A and 7B, laboratory results show that good operating frequencies for $f_1$ and $f_2$ are found in the 100 KHz range±500%, and good values for the coils $L_1$ and $L_2$ tend to be in the 100 uH range±200%

FIG. 8 depicts a third embodiment of a testing device for testing bolt-holes in laminate structure. As with the device of FIGS. 6A and 6B, the testing device 810 shown in FIG. 8, has a first coil 522 and a reference-coil 622 (not shown in FIG. 8), but also has a metal shield 822 covering the second coil. The metal shield 822 causes the reference-coil 622 to better match the impedance of the first coil 522 when the first coil 522 is places against a metallic laminate layer. That is, by matching the metal of the shield 822 to that of an laminate layer, a reference-coil can be expected to provide an even better impedance match to a test-coil.

Figure 9:
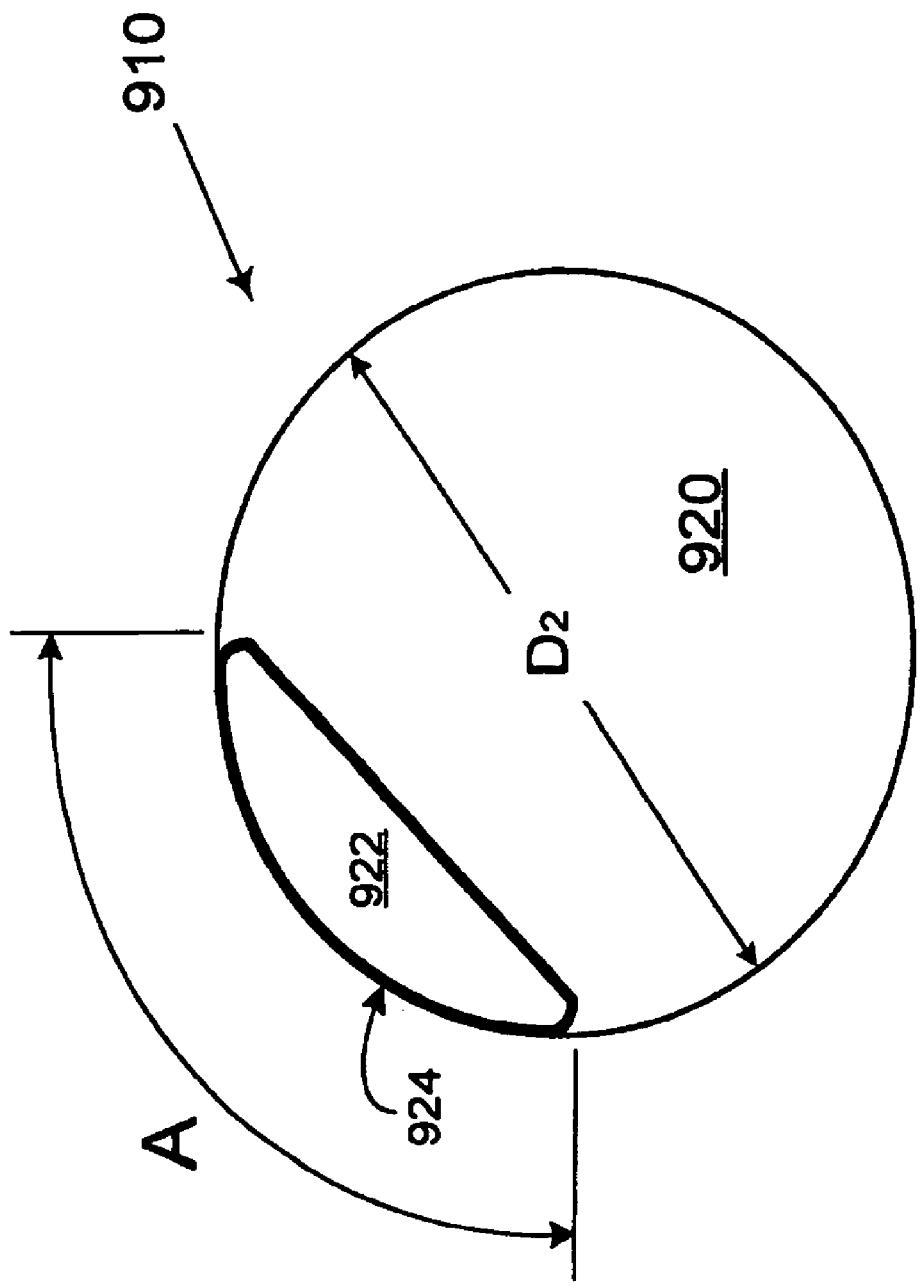
FIG. 9 depicts an exemplary fourth bolt-hole probe.

FIG. 9 depicts a cross-section of a fourth embodiment of a testing device for testing bolt-holes in laminate structure. As shown in FIG. 9, the testing device 910 has a coil 922 that does not circumvent the body 920 but only spans an angular range A. Additionally, although not shown in FIG. 9, the coil 922 may include one or more coils disposed above and/or below the coil 922 that span the angular range A. Accordingly, the coil 922 (with surface portion 924) can detect laminate damage only across range A, which effectively provides the testing device 910 with angular resolution about its cylindrical axis. By placing multiple coils with differing angular ranges, a testing device may simultaneously detect laminate flaws/damage to a particular range about its body.

Figure 10:
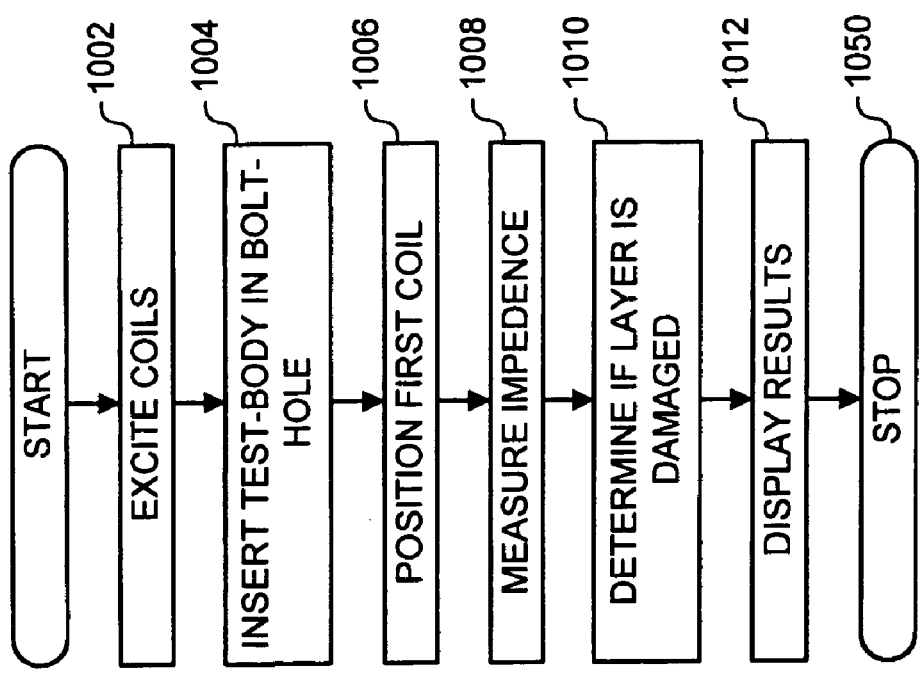
FIG. 10 is a flowchart outlining an exemplary operation for detecting bolt-hole damage.

FIG. 10 is a flowchart outlining an exemplary operation according to the present disclosure for diagnosing a bolt-hole. The process starts at step 1002 where a number of coils in a test-body are excited. As discussed above, the excitation frequency of the coils should can be between 50 KHz and 5 MHz and/or at a frequency to cause the reactive impedance of the coils to be close to that of the characteristic impedance of the circuitry driving the coils. Next, in step 1004, the test-body is inserted into a bolt-hole. Then, in step 1006, the test-body is manipulated such that a first coil of the test-body is positioned in a plane roughly equivalent to the plane of a laminate layer of interest. Control continues to step 1008.

In step 1008, the impedance of the first coil is measured. As discussed above, the impedance of the first coil can be measured against an expected value, a reference value or against the impedance produced by a reference-coil. Next, in step 1010, a determination is made as to whether the laminate layer is flawed/damaged based on the impedance measurement of step 1008. Then, in step 1012, the results of the determination of step 1010 are displayed, and control continues to step 1050 where the process stops.

In various embodiments where the above-described systems and/or methods can in part be implemented using a programmable device, such as a computer-based system or programmable logic, it should be appreciated that the above-described systems and methods can be implemented using any of various known or later developed programming languages, such as "C", "C++", "FORTRAN", Pascal", "VHDL" and the like.

Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform the above-described systems and/or methods.

For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods related to laminate testing.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An apparatus for detecting defects in the proximity of a hole of a laminate structure, the laminate structure having multiple layers, with at least one layer being composed of an electrically conductive material, the apparatus comprising:

a generally cylindrical body portion having a diameter substantially close to the diameter of the hole for insertion into the hole;

a first coil of wire wrapped about the cylindrical body portion such that, when the body portion is inserted into the hole, the first coil of wire resides in a plane substantially parallel to a first electrically conductive layer of the laminate material such that a magnetic field produced by the first coil of wire will produce eddy-currents in the first conductive layer in the plane of the first conductive layer;

a reference-coil coupled to the first coil, the reference-coil having substantially the same electrical properties as the first coil;

a reference shield in close proximity to the reference-coil, wherein the reference shield includes electrical properties substantially identical to the electrically conductive material layer of the laminate structure; and an impedance sensing device coupled to the first coil of wire and the reference-coil, wherein the impedance sensing device electrically excites the first coil and the reference coil to detect an impedance change of the first coil.

2. The apparatus of claim 1, wherein the body portion is primarily composed of a metallic material.

3. The apparatus of claim 1, wherein the body portion is primarily composed of non-metallic material.

4. The apparatus of claim 3, wherein the body portion is primarily composed of a plastic material.

5. The apparatus of claim 1, wherein the first coil and reference-coil are configured in an electrical bridge arrangement.

6. The apparatus of claim 1, wherein both the reference-coil and the first coil are excited by a first frequency, and wherein the impedance of the first coil, and the reference-coil is roughly the same when excited by the first frequency.

7. The apparatus of claim 1, wherein the material of the electrically conductive material is titanium or a titanium alloy.

8. An apparatus for detecting defects in the proximity of a hole of a laminate structure, comprising:

a generally cylindrical body portion having a diameter substantially close in the diameter of the hole for insertion into the hole;

a first coil embedded within the body portion with a surface portion of the first coil residing at or near the surface of the body portion, wherein the surface portion is disposed along less than 360 degrees of a perimeter of the body portion;

a reference-coil coupled to the first coil, the reference-coil having substantially the same electrical properties as the first coil;

a reference shield in close proximity to the reference-coil, wherein the reference shield includes electrical properties substantially identical to the electrically conductive material layer of the laminate structure; and an impedance sensing device coupled to the first coil and the reference-coil to excite the first coil and the reference coil to sense an impedance change in the first coil.

9. The apparatus of claim 8, wherein the surface portion of the first coil is configured to induce eddy currents in a layer of the laminated structure that resides in a common geometric plane with the surface portion, the eddy currents being induced along a portion of a perimeter of the hole corresponding to the surface portion.

10. The apparatus of claim 9, wherein the impedance sensing device includes an output to provide an angular indication of a position of a flaw along a perimeter of the hole in the conductive layer of the laminate structure.

11. A method of diagnosing a crack in the proximity of a bolt-hole of a laminate structure, the laminate structure having multiple layers with at least one electrically conductive layer, the method comprising:

positioning a first coil in the bolt-hole with the first coil residing in a plane substantially parallel to the plane of the electrically conductive layer;

exciting the first coil in a manner as to produce appreciable eddy-currents flowing in the plane of the electrically conductive layer;

exciting a reference coil, wherein the reference coil is in electrical communication with the first coil;

reference shielding the reference coil with a material having electrical properties substantially identical to the electrically conductive material layer of the laminate structure; and measuring the impedance of the first coil as compared to the impedance of the reference coil, wherein the impedance of the first coil changes as a function of eddy-current activity occurring close to the first coil.

12. The method of claim 11, further comprising determining whether a crack exists in the proximity of the hole based on the measured impedance.

13. An apparatus for detecting defects in the proximity of a hole of a laminate structure, the laminate structure having multiple layers, with at least one layer being composed of an electrically conductive material, the apparatus comprising:

a first body;

an emitting means for emitting eddy-currents coupled to the first body;

a reference-emitting means coupled to the emitting means, the reference-emitting means having substantially the same electrical properties as the emitting means;

a reference shielding means in close proximity to the reference-emitting means, wherein the reference shield includes electrical properties substantially identical to the electrically conductive material layer of the laminate structure; and a receiving means coupled to the first body for receiving a signal emitted by the electrically conductive material in response to a signal emitted by the emitting means and reference-emitting means, wherein the emitting means and the receiving means are configured for insertion into the hole.

* * * * *